United States Patent [19]

Bauer et al.

[11] Patent Number: 5,157,202

[45] Date of Patent: Oct. 20, 1992

[54] GAS ABSORPTION FOR SEPARATION OF HYDROCARBONS

[75] Inventors: Heinz Bauer; Hans Becker; Horst Weiss, all of Munich, Fed. Rep. of Germany

[73] Assignee: Linde Aktiengesellschaft, Wiesbaden, Fed. Rep. of Germany

[21] Appl. No.: 658,904

[22] Filed: Feb. 22, 1991

[30] Foreign Application Priority Data

Feb. 24, 1990 [DE] Fed. Rep. of Germany ....... 4005872

[51] Int. Cl.$^5$ ............................ C07C 7/10; C07C 7/00; B01D 19/00
[52] U.S. Cl. .................................... 585/833; 585/862; 585/864; 55/63
[58] Field of Search ...................... 585/862, 864, 833; 55/63

[56] References Cited

U.S. PATENT DOCUMENTS

| | | | |
|---|---|---|---|
| 2,719,601 | 4/1952 | Bartholome et al. | ................... 55/63 |
| 2,838,133 | 6/1958 | Schreiner | ............................ 585/864 |
| 2,891,633 | 6/1959 | Morro, Jr. et al. | ................. 585/864 |
| 3,363,400 | 1/1968 | Takao et al. | ............................. 55/63 |
| 4,134,795 | 1/1979 | Howat, III | .......................... 585/864 |

OTHER PUBLICATIONS

Robinson and Gilliland, *Elements of Fractional Distillation*, 4th Edition, 1950, McGraw Hill Book Company, N.Y.

*Primary Examiner*—Anthony McFarlane
*Assistant Examiner*—Nhat Phan
*Attorney, Agent, or Firm*—Millen, White & Zelano

[57] ABSTRACT

For recovery of low-boiling hydrocarbons by scrubbing, the crude gas mixture which contains low-boiling and high-boiling hydrocarbons, is treated with a scrubbing agent, by which the high-boiling components are scrubbed-out of the gas mixture. The loaded scrubbing agent, with the addition of liquid medium miscible with the scrubbing agent and which reduces the solubility for the scrubbed-out hydrocarbons, is regenerated and the completely regenerated scrubbing agent is recycled to the scrubbing. The regeneration is preferably divided into the following individual steps:

(a) stripping of the loaded scrubbing agent, optionally with addition of medium,
(b) addition of the liquid medium to partially regenerate scrubbing agent, decanting of the split phases,
(c) stripping of the resultant decanted scrubbing agent/medium mixture, and
(d) rectifying the scrubbing agent/medium mixture to separate the scrubbing agent.

29 Claims, 1 Drawing Sheet

GAS ABSORPTION FOR SEPARATION OF HYDROCARBONS

BACKGROUND OF THE INVENTION

This invention relates to a separation process for the recovery of low-boiling hydrocarbons, in which a crude gas containing low-boiling and high-boiling hydrocarbons, is subjected to scrubbing to scrub out the high-boiling components, after which the loaded scrubbing agent is subjected to regeneration and recycled to the scrubbing step.

In the cracking of gas to recover $C_2H_2$ (acetylene), there result as by-products, among others, higher acetylenes, i.e., those with more than two carbon atoms in the molecule. In cracked gas produced by partial oxidation, the percentage of higher acetylenes and higher-boiling components in the crude gas mixture is relatively small; however, in cracked gas produced in an electric arc furnace with the exclusion of oxygen, there are appreciable concentrations of higher acetylenes and other high-boilers, such as aromatics. These heavy, high-boiling components are removed by partial condensation and/or by scrubbing out of the cracked gas.

Both chemical and physical scrubbing agents or combinations thereof are used for the scrubbing operation.

For a physical scrubbing step, a polar scrubbing agent is used for scrubbing a series of higher-boiling components from the crude gas mixture. Known scrubbing agents of this type are, for example, methanol, NMP (N-methylpyrrolidone) and DMF (dimethylformamide).

The regeneration of the scrubbing agent loaded with the scrubbed-out components, optionally takes place by stripping with a stripping gas, by lowering the pressure and/or by raising the temperature of the loaded scrubbing agent, so as to drive out the absorbed components. The regenerated scrubbing agent is then recycled to the scrubbing step.

If the scrubbing agent is loaded with temperature-sensitive unsaturated hydrocarbons, which at higher temperatures tend to polymerize or decompose, it is recommended that the regeneration be conducted only by stripping and/or pressure reduction. But such a process, heretofore, had the drawback that if the vapor pressure of the components dissolved in the scrubbing agent were even, in part, below the vapor pressure of the scrubbing agent, the scrubbing agent could be regenerated by stripping only with great difficulty or incompletely.

SUMMARY OF THE INVENTION

An object of one aspect of this invention is to provide an absorption process that separates high-boiling heavy hydrocarbons, including aromatics reliably, economically, and without adversely affecting the environment, from a crude gas mixture, especially a crude gas mixture containing temperature-sensitive unsaturated hydrocarbons.

Upon further study of the specification and appended claims, further objects and advantages of this invention will become apparent to those skilled in the art.

These objects are attained according to the invention by conducting the regeneration of the loaded scrubbing agent with the addition of a medium which reduces the solubility of the scrubbed-out hydrocarbons. Of particular advantage is the use of a medium which is completely miscible with the scrubbing agent.

A polar scrubbing agent of the type mentioned above is preferably used for the physical scrubbing of a series of high-boiling hydrocarbon components. To achieve complete regeneration according to the invention, the solubility of the scrubbed-out high-boiling components in the scrubbing agent is reduced by the addition of another liquid medium in which the scrubbed-out hydrocarbons are less soluble than in the scrubbing agent. This change in solubility facilitates the regeneration of the scrubbing agent by stripping.

According to a preferred modification of the invention, the regeneration is conducted in several stages, and the aforesaid liquid medium is added in at least one stage. As for the type of liquid medium, it is advantageous to employ a strongly polar medium, for example water, by virtue of which the light components are degassed from the loaded scrubbing agent whereas the mixture of the scrubbing agent and the liquid medium on the one hand form a first liquid phase and the heavy components originally dissolved in the scrubbing agent on the other hand form a second liquid phase, which phases can be separated from one another by decanting.

Thus, the regeneration is preferably performed in at least two stages: the loaded scrubbing agent in the first stage, optionally with addition of the strongly polar medium, is partly freed of dissolved components by stripping and in a second stage, said strongly polar medium is added to the partially regenerated scrubbing agent. In this second stage, some volatile components are desorbed and the fluid is split into at least two liquid phases, a first phase containing scrubbing agent/medium and a second phase containing most of the less volatile components originally dissolved in the scrubbing agent, which phases are separated from one another by decanting. More specifically, by the addition of the strongly polar medium, the highly volatile dissolved components are degassed while heavy hydrocarbons and the scrubbing agent/medium mixture form two separate liquid phases. The latter phases are then separated from one another by decanting or the like.

Since some heavy components can still be dissolved in the mixture of scrubbing agent and medium recovered by decanting, a further regeneration by stripping is advantageously conducted downstream of this stage. In this further regeneration step, components possibly still dissolved in the scrubbing agent/medium mixture are advantageously stripped out with a stripping gas and can also be recovered conventionally.

If only a small amount of stripping gas is available for the total regeneration, the gas mixture recovered in the stripping of the phase containing the scrubbing agent/medium mixture can be advantageously used as stripping gas in the first stage of the regeneration. For the purpose of stripping any available gas is suited which has no adverse effects to the total process. In general nitrogen or a split stream of the purified gas or even air are frequently used stripping gases. In the context of producing acetylene in an electric arc furnace it is especially advantageous to use a recycle stream for stripping which is one of the feed streams to the arc furnace and which consists mainly of hydrogen, methane and ethylene.

To regenerate the scrubbing agent completely for recycling into the scrubbing stage, it is necessary to remove the strongly polar medium from the scrubbing agent/medium mixture. According to another aspect of the invention the scrubbing agent/medium mixture is advantageously separated in a final stage by a rectification.

If the scrubbing agent/medium mixture cannot be stripped completely free of hydrocarbons (because e.g., of lack of stripping gas) then the scrubbing agent/medium mixture to be separated by rectification will contain small portions of hydrocarbons, which will concentrate in the central part of the rectification column. In this case, the concentrated hydrocarbons are removed as one or several side streams by one or more central tap holes and are preferably recycled to the second stage of separation where the decanting step is conducted.

The process according to the invention can be applied to a variety of gas absorption separation processes, especially for the recovery of hydrocarbons. By the multiple stop procedure of the present invention, the components dissolved in the scrubbing agent can be recovered as separate enriched fractions. Also, by adjusting the process parameters (pressure, temperature, amount of stripping gas, etc.), and by the addition of part of the light components, relatively poorly soluble in the scrubbing agent, can be removed so efficiently that the phases recovered in the decanting contain only extraordinarily small portions of highly volatile components. Moreover, the separate steps can advantageously be performed in several substeps with the use of several stripping columns or flash drums in order to obtain finer fractions.

It is appreciated that "high-boiling" and "low-boiling" are relative terms. According to the preferred embodiment of this invention, high-boiling hydrocarbons contain at least 3 carbon atoms per molecule and low-boiling hydrocarbons contain not more than 4 carbon atoms per molecule. It is foreseeable, however that with particular crude gases and particular conditions, this definition would change. Thus, it is sufficient to define the hydrocarbons in accordance with their relative boiling points as opposed to absolute values.

It is likewise appreciated that the term "strongly polar" in describing the medium is also a relative term. It is sufficient, however, that the added medium is more polar than the scrubbing agent so to reduce the solubilities of the hydrocarbons in the scrubbing agent. It is preferred that the added medium be sufficiently polar to be able to split out a separate liquid phase enriched in high boiling components which can be decanted from the scrubbing agent/medium mixture.

BRIEF DESCRIPTION OF THE DRAWING

Various other objects, features and attendant advantages of the present invention will be more fully appreciated as the same becomes better understood when considered in conjunction with the accompanying drawing, in which like reference characters designate the same or similar parts throughout the several views, and wherein:

The attached drawing is a schematic block flowsheet of a preferred comprehensive embodiment of the invention.

DETAILED DESCRIPTION OF THE DRAWING

Figure 1:
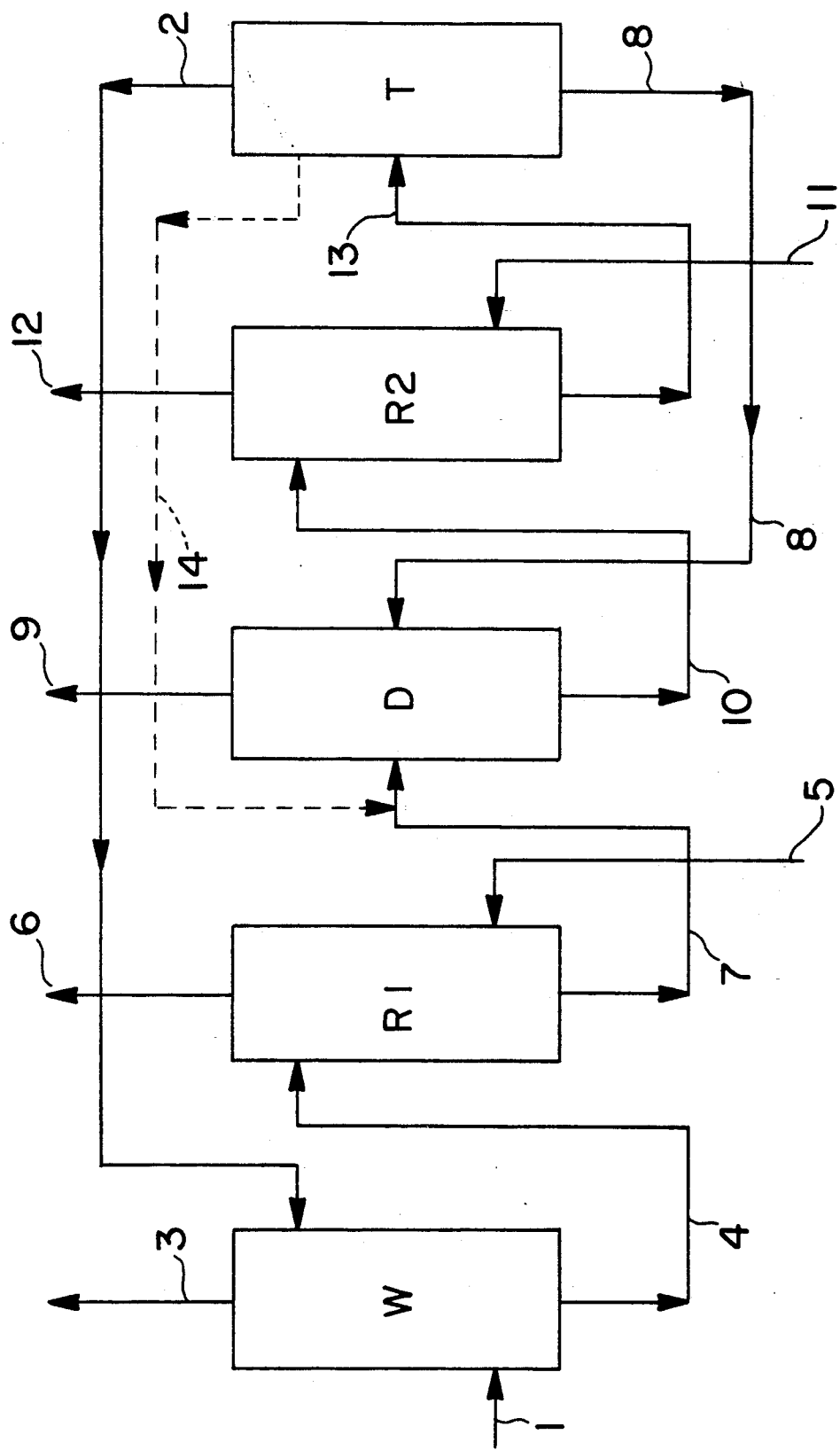

Crude gas 1, which contains the higher boiling components A ($A = A_1 + A_2 + A_3$ in order of boiling points) to be separated, is scrubbed under pressure in a scrubbing column W with a regenerated scrubbing agent 2. At the head of the scrubbing column, a purified gas stream 3 is removed from the components of A to be separated. Scrubbing agent 4, loaded with components A, collects at the bottom of the scrubbing column and is fed to a first coarse regeneration step. Those of components A, which exhibit the poorest solubility in the scrubbing agent, are released from the scrubbing agent in this first regeneration step R1 by release of pressure, heating and/or introduction of a stripping gas 5 and are removed via overhead conduit 6. In this regeneration step, a small amount of the strongly polar medium (not represented here) can optionally be added to the scrubbing agent to facilitate the evolution of the components. If it is desired to fractionate components $A_1$ released during this first regeneration step $R_1$, it is possible to divide $R_1$ into separate substeps (for example by using two or more stripping columns or flash drums). In this way, e.g., low-boiling components, which actually are desired in the purified gas stream, but were coabsorbed by the scrubbing agent in scrubbing column W to a small extent, can be selectively separated from the scrubbing agent and again be admixed with the crude gas.

Partly regenerated scrubbing agent 7, collecting in the first regeneration step, is mixed in a second regeneration step D with a medium 8 having a stronger polarity than the scrubbing agent, which reduces the solubility of remaining components $A_2 + A_3$ in the scrubbing agent/medium mixture to such an extent that the liquid splits into two liquid phases. One liquid phase contains mainly the scrubbing agent/medium mixture and only small amounts of component $A_3$, while the other phase contains virtually all the components $A_2$ and the main portion of the high-boilers $A_3$, which cannot be separated economically by stripping—if at all + and contains only small amounts of the scrubbing agent/medium mixture. The liquid phases are separated from one another by decanting, and phase 9, containing the components $A_2$ and most of $A_3$, is removed.

Scrubbing agent/medium mixture 10, still containing small amounts of component $A_3$, is completely freed in a third regeneration step R2 from components $A_3$ contained therein by stripping with a stripping gas 11 and $A_3$ components are removed overhead in conduit 12. In a fourth regeneration step, the scrubbing agent/medium mixture 13 is separated into: agent 2 and medium 8 by rectification. Completely regenerated scrubbing agent 2 is recycled into scrubbing column W for scrubbing out other components A. Medium 8 is recycled to at least one of the regeneration stages. As indicated by broken line 14, any residual hydrocarbons, possibly accumulating in rectification column T, can be removed and recycled to the second regeneration stage where the partly regenerated scrubbing agent/medium mixture forms two liquid phases which are separated from each other by decantion.

By the above-described four-stage regeneration the scrubbing agent and medium can be completely regenerated, and separated components A can be recovered in fractionated form.

The entire disclosure of of corresponding application Federal Republic of German P 40 05 872.7, filed Feb. 24, 1990, is hereby incorporated by reference.

Without further elaboration, it is believed that one skilled in the art can, using the preceding description, utilize the present invention to its fullest extent. The following preferred specific embodiment is, therefore, to be construed as merely illustrative, and not limitative of the remainder of the disclosure in any way whatsoever.

EXAMPLE

The following table shows with reference to the numbering of the FIGURE the efficiency of the process for the freeing of an acetylene crude gas from higher acetylenes and high-boiling hydrocarbons. The symbols listed below are explained as follows:
- — inert substances— contain components such as $H_2$, $N_2$, $O_2$ or CO;
- — KW 1 — designates non-acetylenic (i.e., saturated and ethylenically unsaturated) low-boiling hydrocarbons having not more than 4 carbon atoms in the molecule;
- — KW 2 — designates all high-boiling hydrocarbons with 5 or more carbon atoms;
- — KW 3 — designates all aromatics.

TABLE

| (all amounts in kg/h) | | | | | | | | |
|---|---|---|---|---|---|---|---|---|
|  | 1 | 3 | 5 | 6 | 9 | 11 | 12 | 14 |
| Acetylene | 5,300 | 5,000 | 0 | 300 | 0 | 0 | 0 | 0 |
| Propyne | 200 | 150 | 0 | 50 | 0 | 0 | 0 | 0 |
| $C_4$ acetylene | 650 | 80 | 0 | 500 | 10 | 0 | 60 | 0 |
| $C_{6+}$ acetylene | 20 | 0 | 0 | 2 | 12 | 0 | 6 | 0 |
| Inert substances | 1,400 | 1,399 | 60 | 61 | 0 | 60 | 60 | 0 |
| KW 1 | 4,200 | 4,030 | 1,100 | 1,270 | 1 | 1,100 | 1,100 | 0 |
| KW 2 | 300 | 0 | 0 | 222 | 70 | 0 | 8 | 30 |
| KW 3 | 300 | 0 | 0 | 100 | 80 | 0 | 120 | 3 |
| T/°C. | 45 | −20 | 40 | 30 | 50 | 40 | 50 | 110 |
| p/bar | 15 | 14 | 2 | 1.5 | 1.5 | 2 | 1.7 | 3.2 |

Scrubbing agent (2): 5,800 kg/h methanol
Polar medium (8): 10,000 kg/h water

From the foregoing description, one skilled in the art can easily ascertain the essential characteristics of this invention, and without departing from the spirit and scope thereof, can make various changes and modifications of the invention to adapt it to various usages and conditions.

In the following claims, the term "loaded scrubbing agent" is intended to mean scrubbing agent containing high-boiling hydrocarbons in saturated or partly saturated concentrations.

What is claimed is:

1. In a gas absorption separation process for recovering low-boiling hydrocarbons, comprising scrubbing a crude gas mixture containing low-boiling and high-boiling hydrocarbons with a scrubbing agent, thereby scrubbing out the high-boiling hydrocarbons from the gas mixture, regenerating resultant loaded scrubbing agent and recycling regenerated scrubbing agent to the scrubbing step, the improvement wherein the regeneration comprises:
    (a) adding to said loaded scrubbing agent a liquid medium which reduces the solubility of the scrubbed-out hydrocarbons in said scrubbing agent and which results in the formation of two separate immiscible liquid phases; and
    (b) separating said two liquid phases from one another by decanting in a decanting step.

2. A process according to claim 1, comprising conducting the regeneration in at least two stages, adding said liquid medium to at least one stage thereby reducing the solubility of the scrubbed-out hydrocarbons.

3. A process according to claim 2, further comprising: stripping said loaded scrubbing agent in a first stage with a stripping gas, optionally with the addition of said liquid medium to partially liberate said scrubbing agent from dissolved components; and adding said liquid medium to resultant partially regenerated scrubbing agent in a second stage, thereby forming said two separate liquid phases, one of said phases comprising a scrubbing agent/medium mixture and the other phase consisting essentially of said high-boiling hydrocarbons.

4. A process according to claim 3, wherein the liquid medium is water.

5. A process according to claim 3, further comprising rectifying resultant scrubbing agent/medium mixture, thereby purifying said scrubbing agent.

6. A process according to claim 5, further comprising collecting a hydrocarbon fraction during said rectifying of the scrubbing agent/medium mixture, and recycling said hydrocarbon fraction into the decanting stage.

7. A process according to claim 3, wherein the low boiling hydrocarbon is a mixture of chemical compounds with acetylene in a predominant concentration.

8. A process according to claim 3, wherein said liquid medium is more polar than said scrubbing agent.

9. A process according to claim 3, further comprising stripping resultant decanted scrubbing agent/medium mixture with a stripping gas to further regenerate said agent/medium mixture.

10. A process according to claim 3, wherein the liquid medium is water.

11. A process according to claim 10, wherein the scrubbing agent is methanol.

12. A process according to claim 10, wherein the low boiling hydrocarbon is a mixture of chemical compounds with acetylene in a predominant concentration.

13. A process according to claim 9, comprising conducting said stripping in the first stage of the regeneration with a stripping gas recovered from the stripping of the scrubbing agent/medium mixture separated from the decanting step.

14. A process according to claim 3, wherein the scrubbing agent is methanol.

15. A process according to claim 1, wherein the liquid medium is miscible with said scrubbing agent and upon adding said liquid medium to said loaded scrubbing agent, the two separate immiscible liquid phases are formed, and one of said phases being enriched in said high-boiling hydrocarbons.

16. A process according to claim 15, wherein the liquid medium is water.

17. A process according to claim 15, further comprising stripping resultant decanted scrubbing agent/medium mixture, thereby further regenerating said agent/medium mixture.

18. A process according to claim 17, wherein the liquid medium is water.

19. A process according to claim 8, further comprising, after said stripping, rectifying resultant scrubbing agent/medium mixture, thereby purifying said scrubbing agent.

20. A process according to claim 14, further comprising collecting a hydrocarbon fraction during said rectifying of said resultant scrubbing agent/medium mixture, and recycling said hydrocarbon fraction to said decanting step.

21. A process according to claim 20, wherein the scrubbing agent is methanol.

22. A process according to claim 17, where the crude gas contains acetylene, higher acetylenic and non-acetylenic hydrocarbons having not more than 4 carbon atoms, and hydrocarbon having at least 5 carbon atoms, and wherein the liquid medium is water.

23. A process according to claim 22, wherein the crude gas is a cracked gas produced in an electric arc furnace.

24. A process according to claim 1, wherein the liquid medium is water.

25. A process according to claim 1, further comprising rectifying resultant scrubbing agent/medium mixture, thereby purifying said scrubbing agent.

26. A process according to claim 25, further comprising collecting a hydrocarbon fraction during said rectifying of said resultant scrubbing agent/medium mixture, and recycling said hydrocarbon fraction into the decanting stage.

27. A process according to claim 1, wherein the scrubbing agent is methanol.

28. A process according to claim 1, wherein the low boiling hydrocarbon is a mixture of chemical compounds with acetylene in a predominant concentration.

29. A process according to claim 1, wherein said liquid medium is more polar than said scrubbing agent.

* * * * *